United States Patent
Ilan et al.

(10) Patent No.: US 10,960,105 B2
(45) Date of Patent: *Mar. 30, 2021

(54) HEMOSTATIC COMPOSITION

(71) Applicants: Omrix Biopharmaceuticals Ltd.; Ethicon, Inc., Somerville, NJ (US)

(72) Inventors: Erez Ilan, Kibbutz Netzer Sereni (IL); Omri Faingold, Ness Ziona (IL); Nataly Freizus, Arad (IL); Ronen Eavri, Binyamina (IL); Dwayne Looney, Flemington, NJ (US); Sridevi Dhanaraj, Raritan, NJ (US); James Galloway, Bridgewater, NJ (US); Walter Danker, Newtown, PA (US)

(73) Assignees: Omrix Biopharmaceuticals Ltd., Rehovot (IL); Ethicon, Inc., Somerville, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/783,403

(22) Filed: Feb. 6, 2020

(65) Prior Publication Data

US 2020/0171201 A1 Jun. 4, 2020

Related U.S. Application Data

(62) Division of application No. 16/167,924, filed on Oct. 23, 2018, which is a division of application No.
(Continued)

(30) Foreign Application Priority Data

Nov. 8, 2015 (IL) .......................................... 242496
Nov. 8, 2015 (IL) .......................................... 242497

(51) Int. Cl.
*A61L 26/00* (2006.01)
*A61L 24/00* (2006.01)
(Continued)

(52) U.S. Cl.
CPC ......... *A61L 26/0023* (2013.01); *A61L 24/001* (2013.01); *A61L 24/0015* (2013.01);
(Continued)

(58) Field of Classification Search
CPC .. A61L 26/0023; A61L 24/02; A61L 26/0004; A61L 24/043; A61L 26/00;
(Continued)

(56) References Cited

U.S. PATENT DOCUMENTS 1,540,979 A 6/1925 Bloom
3,364,200 A 1/1968 Ashton et al.
(Continued)

FOREIGN PATENT DOCUMENTS

AU 2013218367 B2 7/2015
CA 2688196 C 1/2014
(Continued)

OTHER PUBLICATIONS

Cullen, et al., The role of oxidised regenerated cellulose/collagen in chronic wound repair and its potential mechanism of action, The International Journal of Biochemistry & Cell Biology, Apr. 15, 2002, pp. 1544-1556, vol. 34.
(Continued)

*Primary Examiner* — Blessing M Fubara
(74) *Attorney, Agent, or Firm* — David R. Crichton

(57) ABSTRACT

The present invention relates to improved hemostatic compositions comprising cellulose-based fibers supplemented with compounds, preparation and use thereof.

9 Claims, 2 Drawing Sheets

Related U.S. Application Data

15/346,193, filed on Nov. 8, 2016, now Pat. No. 10,137,220.

(60) Provisional application No. 62/252,785, filed on Nov. 9, 2015, provisional application No. 62/252,796, filed on Nov. 9, 2015.

(51) Int. Cl.
*A61L 24/04* (2006.01)
*A61L 24/06* (2006.01)
*A61L 24/02* (2006.01)
*A61L 24/08* (2006.01)

(52) U.S. Cl.
CPC ............. *A61L 24/02* (2013.01); *A61L 24/043* (2013.01); *A61L 24/06* (2013.01); *A61L 24/08* (2013.01); *A61L 26/00* (2013.01); *A61L 26/0004* (2013.01); *A61L 2300/106* (2013.01); *A61L 2300/232* (2013.01); *A61L 2300/25* (2013.01); *A61L 2300/418* (2013.01); *A61L 2300/802* (2013.01); *A61L 2400/04* (2013.01)

(58) Field of Classification Search
CPC ...... A61L 24/08; A61L 24/06; A61L 24/0015; A61L 24/001; A61L 2300/106; A61L 2300/25; A61L 2300/418; A61L 2300/232; A61L 2300/802; A61L 2400/04; A61P 31/00; A61P 7/04; A61P 17/02; A61P 43/00; C08L 1/04
See application file for complete search history.

(56) References Cited

U.S. PATENT DOCUMENTS

| | | | |
|---|---|---|---|
| 4,626,253 A | 12/1986 | Broadnax | |
| 4,637,815 A | 1/1987 | Lemole | |
| 4,749,689 A | 6/1988 | Miyata | |
| 5,180,398 A | 1/1993 | Boardman et al. | |
| 5,403,278 A | 4/1995 | Ernst | |
| 5,484,913 A | 1/1996 | Stilwell | |
| 5,643,596 A | 7/1997 | Pruss et al. | |
| 5,645,849 A | 7/1997 | Pruss et al. | |
| 5,696,191 A | 12/1997 | Nohr | |
| 6,056,970 A | 5/2000 | Greenawalt | |
| 6,225,461 B1 | 5/2001 | Akimoto | |
| 6,309,454 B1 | 10/2001 | Harvey | |
| 6,361,551 B1 | 3/2002 | Torgerson | |
| 6,627,749 B1 | 9/2003 | Kumar | |
| 7,923,031 B2 | 4/2011 | Moeller | |
| 8,021,684 B2 | 9/2011 | Moeller | |
| 8,722,081 B2 | 5/2014 | Filatov | |
| 8,815,832 B2 | 8/2014 | Wang | |
| 8,883,194 B2 | 11/2014 | Bedard | |
| 9,131,929 B2 | 9/2015 | Macphee | |
| 10,034,957 B2 | 7/2018 | Wang | |
| 10,137,220 B2 * | 11/2018 | Ilan | A61P 31/00 |
| 10,137,221 B2 * | 11/2018 | Ilan | A61L 24/08 |
| 2002/0192271 A1 | 12/2002 | Hedner | |
| 2004/0005350 A1 | 1/2004 | Looney | |
| 2006/0233869 A1 | 10/2006 | Looney | |
| 2008/0020026 A1 | 1/2008 | Cochrum | |
| 2008/0027365 A1 | 1/2008 | Huey | |
| 2008/0138387 A1 | 6/2008 | Machiraju | |
| 2009/0062233 A1 | 3/2009 | Ji | |
| 2012/0253298 A1 | 10/2012 | Henderson | |
| 2013/0028975 A1 | 1/2013 | Hedrich | |
| 2013/0310873 A1 | 11/2013 | Stopek | |
| 2013/0316974 A1 | 11/2013 | Wang | |
| 2013/0345678 A1 | 12/2013 | Rubin | |
| 2015/0010612 A1 | 1/2015 | Vogt | |
| 2015/0017225 A1 | 1/2015 | Hubbell | |
| 2016/0074602 A1 | 3/2016 | Wang | |
| 2019/0013959 A1 | 1/2019 | Snyman | |

FOREIGN PATENT DOCUMENTS

| | | |
|---|---|---|
| CN | 1850111 A | 10/2006 |
| CN | 104013991 A | 9/2014 |
| CN | 104321085 A | 1/2015 |
| EP | 0216378 A2 | 9/1986 |
| EP | 0216378 | 4/1987 |
| EP | 1323436 A1 | 7/2003 |
| EP | 1731175 B1 | 9/2009 |
| EP | 2203053 A1 | 7/2010 |
| EP | 2233157 A1 | 9/2010 |
| EP | 1641399 B1 | 9/2012 |
| JP | H07255830 A | 10/1995 |
| JP | H09504719 A | 5/1997 |
| JP | 2002513645 A | 5/2002 |
| JP | 2002/531723 A | 9/2002 |
| JP | 2011/502635 A1 | 11/2011 |
| JP | 2015/505490 A | 2/2015 |
| JP | 2015517388 A | 6/2015 |
| JP | 2018/523440 A | 8/2018 |
| PH | 32014 A | 6/1999 |
| RU | 2235539 C1 | 9/2004 |
| RU | 2009/119264 A | 5/2009 |
| RU | 2522879 | 7/2014 |
| RU | 2522879 C1 | 7/2014 |
| WO | 9013320 A1 | 11/1990 |
| WO | 96/040033 | 12/1996 |
| WO | 9640033 A1 | 12/1996 |
| WO | 0124841 A1 | 4/2001 |
| WO | 0224239 A1 | 3/2002 |
| WO | 2007076415 A3 | 12/2007 |
| WO | 2009091549 A8 | 7/2019 |

OTHER PUBLICATIONS

Howsmon, et al., The Ball-Milling of Cellulose Fibers and Recrystallization Effects, Journal of Applied Polymer Science, Jan. 5, 1959, pp. 313-322, vol. 1 Issue 3.
International Search Report dated Feb. 22, 2017 for International Application No. PCT/IL2016/000019.
International Search Report dated Feb. 22, 2017 for International Application No. PCT/IL2016/000020.
Lazarev, et al., Toxicity of Beryllium and its Compounds, Hazardous Industrial Substances, 1977, pp. 343-344, Reference Book.
Machine Translation ., Hemostatic Composition including hyaluronic acid, https://patents.google.com, May 21, 2009, pp. 1-23, Page Number.
Patent Translate of Description and Claims, Patent Translate of description and claims, Notice, 1986, pp. 1-43, EP0216378.
Rajkhowa, et al., Ultra-fine silk powder preparation through rotary and ball milling, Powder Technology, Jan. 26, 2008, pp. 87-95, vol. 185.
Russian Search Report dated Mar. 6, 2020 for Application No. 2018121030.
Sergeant, et al., Needle-to-suture ratio, as well as suture material, impacts needle-hole bleeding in vascular anastomoses, Interactive CardioVascular and Thoracic Surgery, Feb. 25, 2016, pp. 813-816, vol. 22 Issue 6.
Tomizawa, Clinical Benefits and Risk Analysis of Topical Hemostats: a review, J. Artif. Organs, 2005, pp. 137-142, vol. 8.
Wockhardt UK Ltd., Information for the User, Prosulf Package Leaflet, 2016, 2 pages, none.
Yasnitskii, et al., Oxycelodex, a new hemostatic preparation, Pharmaceutical Chemistry Journal, 1985, pp. 279-281, vol. 18 Issue 4.

* cited by examiner

HEMOSTATIC COMPOSITION

CROSS-REFERENCE TO RELATED APPLICATION

This application is a divisional application of co-pending U.S. application Ser. No. 16/167,924 filed on Feb. 28, 2019, which is a divisional of Ser. No. 15/346,193 filed on Nov. 8, 2016, now Granted U.S. patent Ser. No. 10/137,220 Granted on Nov. 27, 2018, which claims priority to U.S. Provisional Application Ser. No. 62/252,785 filed Nov. 9, 2015 and U.S. Provisional Application Ser. No. 62/252,796 filed Nov. 9, 2015 and claims benefit of Israel Patent Application Serial No. 242496 filed Nov. 8, 2015 and Israel Patent Application Serial No. 242497 filed Nov. 8, 2015, the complete disclosure of which is hereby incorporated herein by reference for all purposes.

FIELD OF THE INVENTION

The present invention relates to improved hemostatic compositions comprising cellulose-based fibers supplemented with compounds.

BACKGROUND OF THE INVENTION

In a wide variety of circumstances, animals, including humans, can suffer from bleeding due to wounds or during surgical procedures. In some circumstances, the bleeding is relatively minor, and normal blood clotting in addition to the application of simple first aid, are all that is required. In other circumstances substantial bleeding can occur. These situations usually require specialized equipment and materials as well as personnel trained to administer appropriate aid. Bleeding during surgical procedures may manifest in many forms. It can be discrete or diffuse from a large surface area. It can be from large or small vessels, arterial (high pressure) or venous (low pressure) of high or low volume. It may be easily accessible or it may originate from difficult to access sites.

Conventional methods to achieve hemostasis include use of surgical techniques, sutures, ligatures or clips, and energy-based coagulation or cauterization. When these conventional measures are ineffective or impractical, adjunctive hemostasis techniques and products are typically utilized.

The selection of appropriate methods or products for the control of bleeding is dependent upon many factors, which include but are not limited to bleeding severity, anatomical location of the source, the proximity of source to adjacent critical structures, whether the bleeding is from a discrete source or from a broader surface area, visibility and precise identification of the source and access to the source.

Many products have been developed as adjuncts to hemostasis. These products include topical absorbable hemostats (TAH) such as oxidized regenerated cellulose, gelatin in various forms with or without a thrombin solution, collagen powder, biologically active topical hemostatic products (topical thrombin solutions, fibrin sealants, etc.), and a variety of synthetic topical sealants.

Topical Absorbable Hemostats (TAHs) are widely used in surgical applications. TAHs encompass products based on oxidized cellulose (OC), oxidized regenerated cellulose (ORC), gelatin, collagen, chitin, chitosan etc. To improve the hemostatic performance, scaffolds based on the above materials can be combined with biologically-derived clotting factors such as thrombin and fibrinogen.

One of the most commonly used topical hemostatic agents is SURGICEL® Original absorbable hemostat, made from oxidized regenerated cellulose (ORC). ORC was introduced in 1960 as a safe and effective hemostatic agent for many surgical procedures. SURGICEL® Original is a loose knit ORC fabric that conforms rapidly to its immediate surroundings and is easier to manage than other absorbable agents because it does not stick to surgical instruments and its size can be easily trimmed. This allows the surgeon to hold the cellulose firmly in place until all bleeding stops.

The control of bleeding is essential and critical in surgical procedures to minimize blood loss, to reduce post-surgical complications, and to shorten the duration of the surgery in the operating room. Due to its biodegradability and its bactericidal and hemostatic properties, oxidized cellulose, as well as oxidized regenerated cellulose have long been used as a topical hemostatic wound dressing in a variety of surgical procedures, including neurosurgery, abdominal surgery, cardiovascular surgery, thoracic surgery, head and neck surgery, pelvic surgery, and skin and subcutaneous tissue procedures. A number of methods for forming various types of hemostats based on oxidized cellulose materials are known, whether made in powder, woven, non-woven, knitted, and other forms. Currently utilized hemostatic wound dressings include knitted, woven, or non-woven fabrics comprising oxidized regenerated cellulose (ORC), which is oxidized cellulose with increased homogeneity of the cellulose fiber.

SURGICEL® absorbable hemostats are used adjunctively in surgical procedures to assist in the control of capillary, venous, and small arterial hemorrhage when ligation or other conventional methods of control are impractical or ineffective. The SURGICEL® family of absorbable hemostats consists of four main product groups, with all hemostatic wound dressings commercially available from Ethicon, Inc., Somerville, N.J., a Johnson & Johnson Company: SURGICEL® Original hemostat is a white fabric with a pale yellow cast and a faint, caramel like aroma. This material is strong and can be sutured or cut without fraying;

SURGICEL® NU-KNIT® absorbable hemostat is similar to SURGICEL® Original but has a denser knit and thus a higher tensile strength, this material is particularly recommended for use in trauma and transplant surgery as it can be wrapped around or sutured in place to control bleeding;

SURGICEL® FIBRILLAR™ absorbable hemostat product form has a layered structure that allows the surgeon to peel off and grasp with forceps any amount of material needed to achieve hemostasis at a particular bleeding site, and therefore, may be more convenient than the knitted form for hard to reach or irregularly shaped bleeding sites. It is particularly recommended for use in orthopedic/spine and neurological surgery;

SURGICEL® SNoW™ absorbable hemostat product form is a structured non-woven fabric that may be more convenient than other forms for endoscopic use due to the structured, non-woven fabric, and is highly adaptable and recommended in both open and minimally invasive procedures.

Another example of a commercial absorbable hemostat containing oxidized cellulose is GELITA-CEL® absorbable cellulose surgical dressing from Gelita Medical BV, Amsterdam, The Netherlands. The commercially available oxidized cellulose hemostat noted above is available in knitted, nonwoven fabrics or powder form. Additional hemostatic products, such as powders consisting of microporous polysaccharide particles and plant starch based particles, are also commercially available as PERCLOT® and ARISTA™.

Other background related references include:

U.S. Pat. Nos. 8,815,832; 3,364,200; US2008/0027365; US2004/0005350; WO2007/076415; U.S. Pat. Nos. 6,627,749; 6,309,454; 5,696,191; 6,627,749; 6,225,461; WO2001/024841A1; EP1,323,436; US2006/0233869. U.S. Pat. Nos. 5,645,849A; 5,643,596A; WO1996040033A1; U.S. Pat. Nos. 5,484,913A; 9,131, 929B2; 8,722,081B2; 7,923,031B2; 6,056,970A; 4,749, 689A; 4,637,815A; US20150017225A1; US20130310873A1; US20120253298A1 US20090062233A1; US20080138387A1; US20020192271A1; EP1641399B1; EP1731175B1; EP2233157A1; EP2203053A1; WO1990013320A1; CA2688196C; AU2013218367B2; CN104013991A; CN1850111A; RU2235539C1; U.S. Pat. No. 5,403,278A; PH32014A; WO2002024239A1.

Howsmon, J. A., & Marchessault, R. H. (1959). The ball-milling of cellulose fibers and recrystallization effects. Journal of Applied Polymer Science J. Appl. Polym. Sci., 1(3), 313-322. doi:10.1002/app.1959.070010308.

Cullen, B., Watt, P. W., Lundqvist, C., Silcock, D., Schmidt, R. J., Bogan, D., & Light, N. D. (2002). The role of oxidised regenerated cellulose/collagen in chronic wound repair and its potential mechanism of action. The International Journal of Biochemistry & Cell Biology, 34(12), 1544-1556. doi:10.1016/s1357-2725(02)00054-7.

Rajkhowa, R., Wang, L., & Wang, X. (2008). Ultra-fine silk powder preparation through rotary and ball milling. Powder Technology, 185(1), 87-95. doi:10.1016/j.powtec.2008.01.005.

Yasnitskii, B. G., Dol'berg, E. B., Oridoroga, V. A., Shuteeva, L. N., Sukhinina, T. V., & Bogun, T. A. (1984). Oxycelodex, a new hemostatic preparation. Pharmaceutical Chemistry Journal, 18(4), 279-281. doi:10.1007/bf00760712.

SUMMARY OF THE INVENTION

The present invention relates to improved hemostatic compositions comprising fibers, originated from a cellulose source material, supplemented with compounds.

In one aspect, the invention provides a hemostatic composition comprising: cellulose-based fibers having a size distribution of D90 of less than 350 μm, and D50 of less than 167 μm, the fibers are at a concentration range of 83.5%-90.0% w/w of the entire composition; an omega amino carboxylic acid at a concentration range of 2.5%-5.0% w/w of the entire composition; protamine salt at a concentration range of 2.5%-5.0% w/w of the entire composition; a divalent cation, the cation concentration being 1.3%-1.8% w/w of the entire composition, wherein the composition is in the form of a powder and/or aggregates.

In some embodiments the composition of the invention also comprises fibers of size 350 μm.

Size distribution D50 is also known as the median diameter or the medium value of the units in the powder/aggregates size distribution, it is the value of the units' diameter at 50% in the cumulative distribution. For example, if D50 is X μm, then 50% of the units in the sample are larger than X μm, and 50% are smaller than X μm. Size distribution is the number of units that fall into each of the various size ranges given as a percentage of the total number of all units' sizes in the sample of interest. Accordingly, D90 value refers to 90% of the units having a size that is smaller than the D90 value. All ranges disclosed herein include the upper and lower limit, where applicable.

In one embodiment, the cellulose-based fibers have a size distribution of D90 of less than 177 μm and D50 of less than 95 μm.

In a further embodiment, the cellulose-based fibers are Oxidized Regenerated Cellulose (ORC) fibers.

In another further embodiment, the omega amino carboxylic acid is Epsilon Amino Caproic Acid (εACA).

In some embodiments, the protamine salt is protamine sulfate.

In some embodiments, the divalent cation salt is provided by calcium chloride.

In some embodiments, the concentration ranges of εACA, protamine sulfate, and calcium chloride are 2.5%-5.0%, 2.5%-5.0%, 5.0%-6.5% w/w, respectively, and wherein the remaining weight is contributed by the cellulose-based fibers to a total weight of 100% w/w.

In some embodiments, a gel formed from the powder composition upon contact with blood has a resistance of equal to or higher than 10 times that of a gel formed upon contact of a comparative powder composition consisting of Oxidized Regenerated Cellulose (ORC) with blood; and/or wherein a gel formed from the aggregates composition has a hemostatic capability of equal to or higher than 1.5 times that of a gel formed upon contact of a comparative aggregates composition consisting of ORC with blood.

In some embodiments, the composition is in the form of aggregates having a size in the range of 75 μm-420 μm.

In another aspect, the invention provides a method for making a hemostatic composition comprising the steps of: mixing cellulose fibers having a size distribution of D90 of less than 350 μm, and D50 of less than 167 μm, the fibers being at a concentration range of 83.5%-90% w/w of the entire composition with the following powder compounds:

i—an omega amino carboxylic acid at a concentration range of 2.5%-5.0% w/w of the entire composition;

ii—protamine salt at a concentration range of 2.5%-5.0% w/w of the entire composition; and iii—a divalent cation, the cation concentration being 1.3%-1.8% w/w of the entire composition.

In some embodiments, the fibers have a size distribution of D90 of less than 177 μm, and D50 of less than 95 μm.

In another aspect, the invention provides a hemostatic composition obtainable according to the method of the invention.

In some embodiments, the method further comprises the steps of: compacting the hemostatic composition; and optionally, subjecting the compacted composition to drying, and size reduction, thereby obtaining hemostatic aggregates.

In another aspect, the invention provides a hemostatic aggregates composition obtainable according to the method of the invention.

In another aspect, the invention provides a method for forming a gel comprising the step of:

contacting a hemostatic powder and/or aggregates composition according to the invention with blood, thereby forming a gel.

In one embodiment, when the contacting is carried out with the powder composition, the formed gel has a resistance of equal to or higher than 10 times that of a gel formed upon contact of a comparative powder composition consisting of Oxidized Regenerated Cellulose (ORC) with blood;

and/or wherein when the contacting is carried out with the aggregates composition, the formed gel has a hemostatic capability of equal to or higher than 1.5 times that of a gel formed upon contact of a comparative aggregates composition consisting of ORC with blood.

In another aspect, the invention provides a gel obtainable by the method according to the invention.

In another aspect, the invention provides a kit comprising a container including a hemostatic composition according to the invention and optionally an applicator, carrier and/or instructions for use.

In another aspect, the invention provides a method of treating a bleeding wound; a bacterial infection at a wound site, minimizing or preventing a leak from an anastomotic site; sealing a leak at a site and/or preventing adhesion at a surgery site in a subject in need, the method comprising applying an effective amount of the hemostatic composition according to the invention onto and/or into the wound and/or site of the subject.

The subject can be a human patient or an animal.

In another aspect, the invention provides use of a hemostatic composition according to the invention for the treatment of a bleeding wound; a bacterial infection at a wound site, minimizing or preventing a leak from an anastomotic site; sealing a leak at a site and/or preventing adhesion.

In one embodiment, the use is for minimizing or preventing a leak in a coronary artery bypass graft (CABG) surgery.

In one embodiment the application is carried out without applying pressure on the composition towards the wound and/or site. For example manual compression using a gauze is not necessary. In various products the product requires manual compression during application for at least a minute. The advantage of using the hemostatic composition without compression is that the hemostatic composition can be applied in/on hard to reach areas.

DETAILED DESCRIPTION

Figure 1:
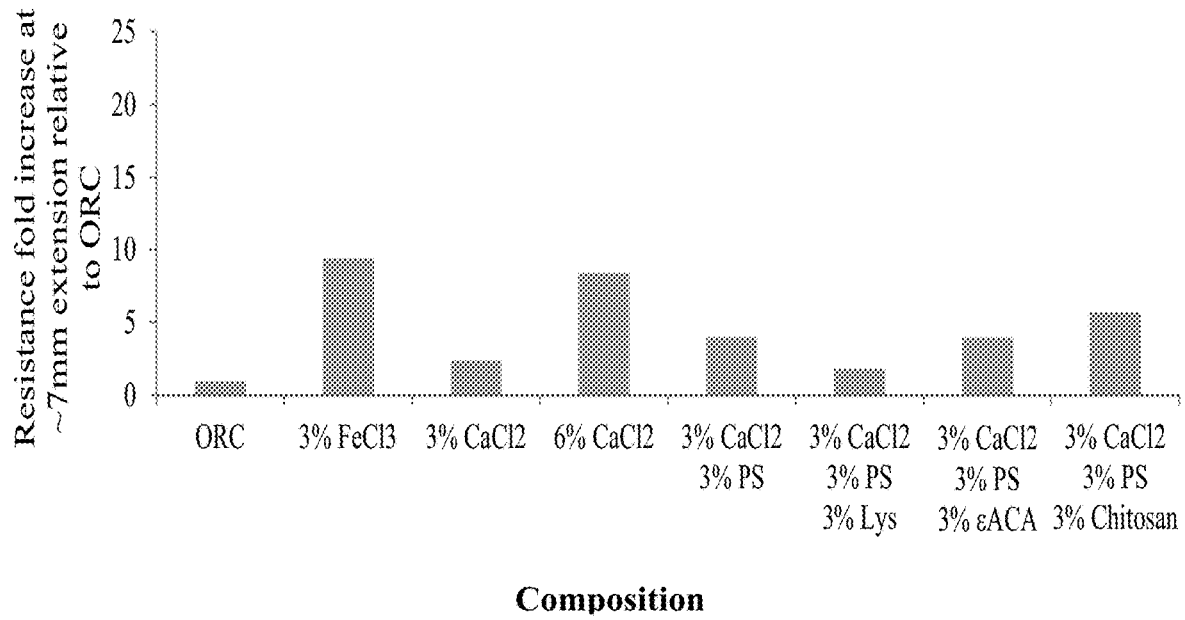
FIGS. 1 and 2 are bar graphs showing the resistance force/cohesive strength obtained from the different powder compositions using a modified Bloom test. The resistance force obtained from non-supplemented fine ORC fibers served as a baseline for the entire experiment.

The invention relates to improved hemostatic composition(s), in powder and/or aggregates form, comprising cellulose-based fibers, supplemented with compounds.

The invention relates to powder and/or aggregates composition(s) having surprising physical properties and highly beneficial effect(s) for hemostasis upon gel or clot formation; to their preparation and use thereof. For example, the powder and/or aggregates composition induce gel or clot formation having beneficial physical properties, such as increased cohesive strength, and beneficial hemostatic capability.

The hemostatic composition comprises fibers originated from a cellulose-based material and supplemented with compounds; the composition is in the form of powder and/or aggregates.

The term "cellulose-based fibers" relates to fibers comprising a cellulose backbone. The cellulose backbone can be modified, for example, it may include alterations in carboxylation or oxidation levels. Non limiting examples of cellulose-based materials include oxidized cellulose or oxidized regenerated cellulose, Carboxymethyl cellulose, Hydroxyethyl cellulose, Hydroxypropyl cellulose and Methylcellulose.

Non limiting examples of cellulose-based fibers are ORC fibers, Cotton fibers, Rayon fibers, and Viscose fibers.

Cellulose-based fibers can be made from cellulose-based materials. Non limiting examples of cellulose-based materials are woven, non-woven, knitted, and/or other forms of fabrics.

The term "fibers" relate to structures having elongated threadlike form.

The term "powder" relates to dispersed dry solid particles.

In one embodiment, a powder composition according to the invention includes fibers and supplementary compounds in particulate form.

The term "aggregates" relates to compacted cellulose-based material, such as powder and/or fibers, having a target size range e.g. the compacted material is subjected to size reduction such as milling and optionally sieving. In one embodiment aggregates are compacted powder composition subjected to size reduction such as milling.

Non limiting examples of size reduction are milling, grinding, shredding and/or tearing.

The term "hemostatic" relates to the ability to reduce bleeding intensity or to arrest bleeding.

The hemostatic composition can be prepared by mixing cellulose-based fibers with omega amino carboxylic acid, protamine salt, and a divalent cation in ranges according to the invention.

Omega amino carboxylic acid can be as ω-carboxylic acid with variable chain lengths including but not limited to 2-aminoaceticacid (glycine), 3-aminopropanoic acid, 4-amino butanoic acid, 5-aminopentanoic acid, 6-aminohexanoic acid 7-aminoheptanoic acid, 8-amino octanoic acid, 9-aminononanoic acid, 10-aminodecanoic acid, and ε aminocaproic acid.

In one embodiment of the invention the protamine salt in the composition is protamine sulfate. Other examples of protamine salts include, but are not limited to, protamine amine.

In one embodiment of the invention, the divalent cation in the composition is provided by calcium chloride. Other examples of divalent cation salts include, but are not limited to, magnesium chloride, calcium acetate and iron(II) chloride.

In one embodiment of the invention the concentration ranges of εACA, protamine sulfate, and calcium chloride are 2.5%-5.0%, 2.5%-5.0%, 5.0%-6.5% w/w, respectively, and the remaining weight of the composition is contributed by the cellulose-based fibers to a total weight of 100% w/w.

The hemostatic composition can further comprise an additive selected from the group consisting of carboxymethyl cellulose, an anti-infective agent, another hemostasis promoting agent, gelatin, collagen, or combinations thereof.

In some embodiments of the invention, the hemostatic compositions further includes carboxymethyl cellulose (CMC) or other polysaccharides, anti-infective agents, hemostasis promoting agents, gelatin, collagen, or combinations thereof.

Non limiting examples of fibers' source material or cellulose-based material to be used as a starting material to make the fibers for the composition include: oxidized regenerated cellulosic fabric, oxidized regenerated cellulose (ORC), woven, knitted, non-woven fabric, shredded oxidized regenerated cellulosic material or combinations thereof.

According to the invention it was found that cohesive strength of a gel induced by ORC fibers is affected by supplementation with compounds as measured by a modified Bloom test.

Results of the modified bloom test demonstrate the force required by a metallic rod to pass through the gel at extension of 7 mm whilst moving at a speed of 5 mm/min. This force reflects the level of resistance of the gel (the greater the force, the greater the resistance of the gel) and in turn indicates what is the level of cohesive strength of a gel. Cohesive strength represents the strength by which molecules of a composition are bound together. The more force required for the rod to proceed with its steady movement, the greater the resistance of the gel is.

It was also found that supplementation of ORC fibers with either 3% or 6% calcium chloride ($CaCl_2$) increased the resistance force in a dose dependent manner.

The findings according to the invention showed that supplementation of ORC fibers with 3% ferric chloride ($FeCl_3$) had a significant positive effect on the resistance of the formed clots.

When comparing the efficacy of 3% $CaCl_2$ supplementation with compositions having positive charges that were further supplemented with either 3% PS; or 3% PS and 3% εACA; or 3% PS and 3% chitosan, the results indicated that there was an improvement in the resistance force of the further supplemented compositions. However it was found that including 3% lysine (Lys), which is another compound having positive charges in the composition, had a negative effect and decreased the resistance force obtained.

Without being bound by the mechanism, supplementing ORC fibers with specific positively charged compounds (e.g. different cations e.g. divalent cations provided by $CaCl_2$, protamine salt e.g. protamine sulfate or positively charged polysaccharide e.g. chitosan and an omega amino carboxylic acid e.g. εACA) may increase the cohesive strength of a gel formed by the hemostatic powder composition.

It was also found that supplementation of ORC fibers with either 3% chitosan or 3% PS, further to 6% $CaCl_2$ supplementation, showed an increase in the clots' resistance force.

Also, further supplementation of the 6% $CaCl_2$ ORC composition with 3% εACA decreased the resistance of the clots.

In addition, it was found that the improved resistance force demonstrated in clots formed by supplementation of 6% $CaCl_2$, was abolished in clots formed by supplementation of 6% $CaCl_2$ mixture with Lysine (Lys). Also, supplementation of 6% $CaCl_2$—ORC with Arginine (Arg) had the same negative effect.

It was found that superior results in cohesive strength were obtained with ORC supplemented with 5.0% $CaCl_2$, 2.5% PS and 2.5% εACA.

These surprising findings show that supplementing ORC fibers with specific positive compounds and specific combinations and concentrations thereof improves the cohesive strength properties of a gel.

Also, it was found that supplemented ORC fibers (with 5.0% $CaCl_2$, 2.5% PS and 2.5% εACA, a combination that exhibited superior cohesive strength) in the form of aggregates had superior hemostatic capabilities. A positive contribution of calcium chloride to the hemostatic efficacy of the supplemented ORC aggregates was observed.

Aggregates of the ORC fibers, with or without supplementation with different concentrations of compounds, were explored in vivo for their hemostatic effect. The tested compound-supplemented aggregates included fiber combinations of 10.0% (w/w of the final mixture weight) long ORC fibers and 77.5-80.0% fine ORC fibers. In each experiment, fine ORC aggregates (without any supplementation) served as a comparative composition to examine the hemostatic efficacy of the compounds to ORC fibers. Success rates of complete bleeding arrest/complete hemostasis were measured. In vivo results reaffirmed that all three compounds (calcium chloride, PS and εACA) are necessary for improving the hemostatic efficacy of ORC fibers and that for both PS and εACA a superior supplementation range is 2.5% to 5.0% and for calcium chloride 5.0% to 6.5% (a cation concentration range of 1.363%-1.636% w/w).

The results showed that the supplemented ORC can be at least 1.5 times more efficient than an ORC comparative composition (37.5% complete hemostasis rate for supplemented ORC vs. 25% complete hemostasis rate for ORC alone). In one aspect of the invention, the composition comprises cellulose-based fibers that have a size distribution of D90 of less than 350 µm, and D50 of less than 167 µm, the fibers are at a concentration range of 83.5%-90.0% w/w of the entire composition and are supplemented with the following compounds: an omega amino carboxylic acid at a concentration range of 2.5%-5.0% w/w of the entire composition; protamine salt at a concentration range of 2.5%-5.0% w/w of the entire composition; a divalent cation salt, the cation concentration in the salt being 1.3%-1.8% w/w of the entire composition. The composition can be in the form of a powder and/or aggregates.

Non limiting examples of Omega amino carboxylic acid include ω-carboxylic acid with variable chain lengths including but not limited to 2-aminoacetic acid (glycine), 3-aminopropanoic acid, 4-amino butanoic acid, 5-aminopentanoic acid, 6-aminohexanoic acid 7-aminoheptanoic acid, 8-amino octanoic acid, 9-aminononanoic acid, 10-aminodecanoic acid, and E aminocaproic acid.

In one embodiment of the invention, the omega amino carboxylic acid is epsilon amino caproic acid (εACA).

In one embodiment of the invention the protamine salt is protamine sulfate.

In one embodiment of the invention the divalent cation salt is provided by calcium chloride.

In one embodiment of the invention the concentration ranges of εACA, protamine sulfate, and calcium chloride are 2.5%-5.0%, 2.5%-5.0%, 5.0%-6.5% w/w, respectively, and the remaining weight of the composition is contributed by the cellulose-based fibers to a total weight of 100% w/w.

The hemostatic composition can further comprise an additive selected from the group consisting of carboxymethyl cellulose, an anti-infective agent, another hemostasis promoting agent, gelatin, collagen, or combinations thereof.

In some aspects of the invention, the hemostatic compositions further includes carboxymethyl cellulose (CMC) or other polysaccharides, anti-infective agents, hemostasis promoting agents, gelatin, collagen, or combinations thereof.

In one embodiment of the invention, the compound comprises protamine sulfate, calcium ions, and ε-aminocaproic acid [5% $CaCl_2$, 2.5% PS and 2.5% epsilon-aminocaproic acid (εACA)].

Non limiting examples of cellulose-based fibers are ORC fibers, Cotton fibers, Rayon fibers, and Viscose fibers.

In one aspect, the invention provides methods for making the compositions of the invention. The compositions have beneficial hemostatic properties and may have wound healing, and other therapeutic properties.

In one embodiment the method comprising the steps of: mixing cellulose-based fibers having a size distribution of D90 of less than 350 µm, and D50 of less than 167 µm or of a size distribution of D90 of less than 177 µm, and D50 of less than 95 µm, the fibers being at a concentration range of 83.5%-90.0% w/w of the entire composition with the following powder compounds:

i—an omega amino carboxylic acid at a concentration range of 2.5%-5.0% w/w of the entire composition;

ii—protamine salt at a concentration range of 2.5%-5.0% w/w of the entire composition; and iii—a divalent cation, the cation concentration being 1.3-1.8% w/w of the entire composition.

In one embodiment, the fibers in the hemostatic compositions according to the present invention are made from oxidized cellulose-based fiber materials and/or from pre-shredded oxidized cellulose-based materials. In another embodiment the fibers in the hemostatic compositions according to the present invention are made from oxidized regenerated cellulose-based fiber materials and/or from pre-shredded oxidized regenerated cellulose-based materials.

The cellulose-based fiber starting material for making the hemostatic composition can include absorbable woven or knitted fabric or non-woven materials comprising cellulose-based material, in particular oxidized cellulose and the neutralized derivatives thereof. For example, the cellulose-based material may be carboxylic-oxidized or aldehyde-oxidized cellulose. Oxidized regenerated polysaccharides including, but without limitation, oxidized regenerated cellulose (ORC) may be used. Oxidized regenerated cellulose is of advantage due to its higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents of each of which are hereby incorporated by reference as if set forth in its entirety.

Examples of cellulosic based materials that may be utilized to prepare fibers of the composition include, but are not limited to, INTERCEED® absorbable adhesion barrier, SURGICEL® Original absorbable hemostat, SURGICEL® NU-KNIT® absorbable hemostat, SURGICEL® FIBRILLAR™ absorbable hemostat, SURGICEL® SNoW™ absorbable hemostat.

The cellulose-based material, e.g. cellulose-based fabric, can be milled to obtain fibers that have a size distribution of D90 of less than 350 µm and of D50 of less than 167 µm. If desired, the milling step can be repeated to obtain a size distribution of D90 of less than 177 µm, and D50 of less than 95 µm.

In one embodiment, the fibers for making the hemostatic composition are prepared by milling a cellulosic source material; the milling step is preceded by forming material pieces by slitting and cutting the cellulosic source material. In this embodiment the milling step is a two-part process with the second part performed in an air classifier wherein the second part can be repeated three times. After a first pass (time) in the air classifier, the resulting "long fibers" have a size distribution of D90 of less than 350 µm and D50 of less than 167 µm. After 3 passes (3 times) in the air classifier the resulting fine ORC fibers have a size distribution of D90 of less than 177 µm and D50 of less than 95 µm.

In one embodiment of the invention, the "fine or short" cellulose-based fibers in the composition have a size distribution of D90 of less than 177 µm, and D50 of less than 95 µm.

The cellulose-based material can be mixed or supplemented with the compounds before, during and/or after the milling steps.

In one embodiment, the hemostatic powder compositions according to the invention comprising the fibers and the compounds are further subjected to steps of compaction, to form aggregates, optionally further comprising the steps of drying, milling/grounding and sieving.

The present invention also relates to hemostatic compositions in the form of aggregates e.g. including compounds and cellulose-based material that have been milled, optionally humidified, compacted, and dried.

In one embodiment, the invention relates to hemostatic composition in the form of aggregates composed of a plurality of interconnected individual cellulose-based fibers and compounds according to the invention that are in aggregate form and e.g. have a diameter along its longest axis that is less than about 420 µm and greater than about 75 µm.

In another aspect, the invention relates to a method of making a plurality of hemostatic aggregates composition comprising the steps of: compacting the hemostatic powder composition and forming aggregates.

In one embodiment of the invention, the method further comprises the steps of: compacting the hemostatic composition; subjecting the compacted composition to drying, milling; and sieving, thereby obtaining hemostatic aggregates.

Aggregates can be made by: optionally including a step of humidifying the hemostatic powder composition; compacting, e.g. by roller and/or slugging, the powder to form hemostatic aggregates; dehumidifying; milling; sieving the hemostatic aggregates; and optionally dosing the resulting hemostatic aggregates into storage containers or into delivery devices.

Before compacting, the powder can be humidified to a water content level of between 11.0% and 16.0% by weight. The powder can be roller compacted or slugging compacted and then subjected to pre-breaking, dehumidification, and subsequently followed by a step of final milling and possibly sieving.

In one embodiment, the powder is compacted at a roller pressure of at least 130 bars. The powder can be compacted at a roller force of at least 26 kN/cm.

The resulting aggregates are selected to a targeted hemostatic aggregate fraction, e.g. by sieving. The targeted aggregates may have dimensions along their longest axis of 75-500 µm such as 75-420 µm. The hemostatic aggregates, intended for dosing, may have moisture content e.g. when measured by "loss on drying" method of less than about 5%, more preferably less than 2%.

Powder compaction can be carried out using the powder according to the invention and a manual hydraulic press (Specac Ltd. Atlas 15 tons model GS15011) and a suitable evacuable pellet die. The pellet die can have a diameter of 10 mm (Specac Ltd. GS03100) to obtain a capsule. The capsule can be released from the pellet die and broken to increase surface area for the next drying step. Broken capsule can be dried in a vacuum oven (Cole-Parmer vacuum oven models 05017-05) at 37° C. for approximately 16 hours to remove any excess humidity (and reach a humidity of less than 5% w/w). The dried broken capsule can be ground/milled e.g. at 20,000 rpm for 30 seconds using IKA® tube mill control 9737790. In a next step, the milled capsules can be vigorously sieved using an MRC (manufacturer) sieve shaker (model LS-200 at an intensity level 2) for 1 minute through a set of 2 sieves; e.g. one with a pore size of 420 µm and another with a pore size of 75 µm. The milled capsules remaining between the two sieves can be collected. In the collected granules/aggregates the fibers and compounds are homogenously distributed.

In one embodiment according to the invention, compositions in the form of aggregates are made directly from cellulose-based fabrics, without a milling step before compaction or without using powders according to the invention as a starting material. For example, cellulose-based fabrics are subjected to compaction and then to drying, milling/grounding and sieving as described above. Supplementation with the compounds can be carried out before, during and/or after compaction.

In one embodiment, making a hemostatic aggregate composition comprises the steps of mixing 83.5%-90.0% w/w cellulose-based fibers; an omega amino carboxylic acid at a concentration range of 2.5%-5.0% w/w of the entire composition; protamine salt at a concentration range of 2.5%-5.0% w/w of the entire composition; and a divalent cation, the cation concentration being 1.3%-1.8% w/w with; and subjecting the mixture to compaction; and optionally drying, milling, and sieving the mixture; thereby obtaining said aggregates.

One or more peptides having positive charges can be further added to the compositions according to the invention. Non limiting examples of such peptides are: abaecin, apidaecins, prophenin, indolicidin, melittin, magainins, LL-37, Bovine lactoferricin, Human lactoferricin, Cecropin A1, Buforin II, Thanatin, Polyphemusin 1, Magainin 2, Human β-defensin-2, Rabbit kidney defensin. Penetratin/Antenapedia, TAT, SynB1, SynB3, PTD-4, PTD-5, FHV Coat-(35-49), BMV Gag-(7-25), HTLV-II Rex-(4-16), D-Tat, R9-Tat Transportan, MAP, SBP, FBP, MPG, MPG (ΔNLS), Pep-1, Pep-2.

One or more polysaccharides having positive charges can be further added to the compositions according to the invention. Non limiting examples of polysaccharides having positive charges are chitosan and cationic guar gum.

Positive cations can be added, such as cations from $FeCl_3$.

In one embodiment manufacturing process starts with ORC material, such as SURGICEL® Original absorbable hemostat, which is cut into 2.54-5.08 cm (1-2 inch) wide sections before the material is fed into a blade that cuts the fabric into smaller pieces. The cut ORC fabric pieces are then ground into ORC fine fibers by two consecutive milling processes (hammer milling and air classifier milling). In an alternative embodiment, the cut ORC fabric pieces are converted directly into fine fibers in a ball mill.

The resulting ORC fine fibers are then humidified to between about 11% w/w and about 16% w/w as measured by Ohaus halogen moisture analyzer and then roller compacted into large aggregates. Prior to compacting, whether be it before or after milling, the fibers are supplemented with the compounds of the inventions in the form of particles and in a suitable concentration.

The term "particles" relates to a substance that is composed of dispersed solid materials.

The humidifying step could be omitted if a sufficient amount of hygroscopic compound such as calcium chloride is mixed with the ORC fibers. Sufficient amount of hygroscopic compound is, for example, an amount that allows humidification to a level of between about 11% and about 16% as measured by Ohaus halogen moisture analyzer.

The term "hygroscopic material" relates to a substance that is capable of attracting and holding water molecules from the surrounding, usually at normal or room temperature environment. Non limiting examples include zinc chloride, calcium chloride, potassium hydroxide and sodium hydroxide.

The moisture analyzer operates on a thermogravimetric principle wherein the moisture analyzer determines the weight of the sample; the sample is then quickly heated by the integral halogen dryer unit and moisture vaporizes. During the drying operation, the instrument continuously determines the weight of the sample and displays the result. Upon completion of drying, a tabulated result is displayed as percent moisture content, percent solids, weight or percent regain, in particular, the analyzer tests between 0.5 gr-1.0 gr of aggregates with a 4 minute ramp, 90° C. *maximum* temperature and the following settings: Test ID—LOD; Profile—Standard; Dry Temperature—90° C.; Switch Off—A60; Result—Moisture %; Custom—Off; Target Weight—None.

Typically, sieving is carried out to separate target aggregates/granules between the size of 75 μm and 420 μm as determined by screen sieving.

In one embodiment, excess moisture introduced for purposes of compaction is removed by a dehumidification or drying process. After compaction, milling and sieving steps, the composition is dosed into applicator devices. Then the composition in the device is subjected to packaging and sterilization.

In one embodiment, storage moisture prior to dosing into an applicator is less than about 2% at conclusion of drying to achieve preferably less than 6% moisture content in controlled environment (0.3-0.6%/hr per 500 gram sample moisture gain depending on relative humidity, commonly 25-55% relative humidity) for dosing into applicators.

One process for manufacturing the hemostatic aggregates comprises, for example, the steps of:

(a) providing a cellulose-based (cellulose source) material and optionally, slitting and cutting the cellulose-based material;

Optionally, (b) reducing the size (e.g. by milling in an air classifier) of the material from step a) to obtain long fibers;

(c) reducing the size (e.g. by milling in an air classifier) of the material from step a) or b) to obtain fine fibers;

optionally, (d) mixing long and fine fibers to obtain mixed fibers;

(e) supplementing the fibers from step c) or d) with the compounds to obtain compound-supplemented fibers;

optionally, (f) humidifying the compound-supplemented fibers obtained in step e) to obtain compound-supplemented humidified fibers;

(g) compacting the compound-supplemented humidified fibers of step f) (e.g. by slugging or rolling) including dehumidification/drying and optionally, reducing size;

(h) sieving;

optionally, (i) dosing into storage containers or into delivery devices, primary packaging and secondary packaging; and optionally, (j) sterilizing.

In one embodiment, the humidifying step could be omitted if a sufficient amount of a hygroscopic compound such as calcium chloride is added to the fibers.

Slitting and cutting can preferably be performed to slit and cut fabric into appropriate size pieces that are between approximately 2.54 cm by 7.62 cm or 5.08 cm by 7.62 cm (1 inch by 3 inches or 2 inches by 3 inches), though smaller pieces can also be used. The main operations performed for slitting and cutting are to unwind a roll of fabric, slit the fabric into strips, cut the strips to size and deliver the cut pieces into the first milling step. A number of cutting and slitting machines are known and commercially available, such as AZCO Model FTW-1000 available from AZCO.

Supplementation with the components can be carried out before or after slitting and cutting the fabric.

In one embodiment, in the first milling step, processed pieces of cellulose fabric are converted from a coarse fiber produced in the slitting and cutting step to a material having a D90 value of less than 452 µm and D50 value of less than 218 µm, while having minimal impact on the color index and water soluble content of the material. A number of machines for milling are commercially available, such as Models DASO6 and WJ-RS-D6A manufactured by Fitzpatrick, which are hammer mill type milling machines, equipped with a 497 µm round screen and a set of blades that break down the fabric until it passes through the screen to produce coarse cellulose fibers. In an exemplary processing run, mill speed can be about 7000 RPM; processing temperature at less than 80° C.; number of blades as 8 (2 impellers each); blade type as a 225 knife, impact type blades; blade orientation set as "impact".

At this stage, the size of the coarse fiber produced in the first milling step can be further reduced to a D90 value of less than 177 µm and a D50 value of less than 95 µm while keeping minimal impact on the color index and water soluble content of the material. A number of machines are available for the second milling step, such as an Air Classifier/F10 Quadro Fine Grind from Quadro.

Coarse fiber from the first milling step can be fed at a controlled rate into the second mill and passed through two milling chambers that are separated by a milling screen. The material can be pulled through the milling chamber by an air blower. The coarse fiber can be processed through the air classifier equipment three times in order to obtain a fine fiber size. At the end of the second milling step, the fine fibers can be collected.

In an exemplary processing run, a Quadro Air Classifier F10 can be used in the second milling step with a milling speed of 8400 rpm, blower speed of 1800 rpm and 3 passes. ORC fine fiber can also be produced in one step by ball milling instead of the two milling steps as described above. In an alternative ball milling embodiment, 50 g of pre-cut ORC fabric, pieces of about 5.08 cm by 5.08 cm (2 inch×2 inch), is ball milled with 12 high-density Zirconia (zirconium dioxide ZrO2, 20 mm in diameter; Glen Mills Inc., Clifton, N.J., USA) by placing the balls and the samples in a 500 mL grinding jar. The jar is clamped into the latching brackets and then counterbalanced on the planetary ball mill PM100; Retsch, Inc., Newtown, Pa., USA). The milling is then performed bi-directionally at 450 rpm for 20 minutes.

Following the milling process, the resulting cellulose-based fine fibers can be humidified to moisture content in the range of about 11% to about 18%, or between about 11% and about 16%, or about 12-16% for the subsequent processing, including e.g. a roller compaction process. Humidity chambers suitable for the humidification step are commercially available e.g. Model CEO-916-4-B-WF4-QS by Thermal Product Solutions. Humidification of chamber air is achieved by water vapor injection. The typical steady-state temperature of 25° C. can be utilized, while the humidity level can be cycled between 75% and 85%, with a preferred target of 85% air humidity. Humidification time or residence time of the material inside the humidity chamber can range from several hours to several days depending on the quantity of the material and air recirculation. In a typical cycle, the material will have 12-13 hours residence time for about 3,000 grams of cellulose-based fine fibers arranged in several trays and exposed to 85% relative humidity and a target of 12% moisture content of the powder after humidification.

The roller compactor compacts the feed of humidified fine ORC fibers, which are then subjected to pre-breaking, dehumidification, final milling and sieving in a screener to obtain the desired hemostatic aggregates sizes.

Typically, supplementation with compounds according to the invention is carried out before compaction and/or before aggregates are produced.

Compaction equipment is known and commercially available. Fibers could be compacted by slugging machinery or any other compaction technique known in the art. Exemplary compaction units are the Fitzpatrick Chilsonator IRR220-L1A with Retsch manual sieving AS200 Screener and the Fitzpatrick Chilsonator CCS220/M3B & RV-M5A with Screener Sweco Vibro-energy unit integrated under M5A. The compaction processing can be performed using two separate subsystems that are bound by a common electrical system. For example, a first subsystem (Roller Compactor: main unit) can be the Fitzpatrick Chilsonator CCS220 roller compactor and the M3B mill for pre-breaking the compacted material, while the second subsystem (Roller Compactor: secondary milling unit) is M5A mill for the final milling with a Sweco or Retch screener for the separation to obtain the desired size aggregates.

Humidified fine cellulose-based fibers can be fed into the hopper of the roller compactor unit, first passed through a main milling unit and then proceed on through a second milling unit. A container can be provided that captures the pre-broken cellulose-based material resulting from the main milling unit. The pre-broken pieces of cellulose-based material can then be fed into the secondary milling unit, which performs the final milling and screening utilizing a screen mesh. The resulting milled cellulose-based material is preferably separated into "fines" (<75 µm), "targets" (75-420 µm), and "overs" (>420 µm) using a screen mesh, such as the Sweco or Retch screener described above.

Moisture is removed from hemostatic aggregates that are obtained following compaction and sieving in a dehumidification or drying step. The dehumidification or drying step preferably does not significantly affect any other product quality attributes, such as color, bulk density and size. Typically, the fibers can be dried as a batch using a conventional fluidized air bed. The resulting dried aggregates can be packed and stored in sealed foil pouches. Dehumidification equipment is known and commercially available. An exemplary bench-top fluidized air bed is commercially available from Retsch (TG-200) with 6 L capacity. Alternatively, a fluidized bed Model No. 0002 from Fluid Air (Aurora, Ill.) can also be used.

In further aspects of the present invention, the hemostatic compositions in the form of powder and/or aggregates can be combined with various additives to further improve the hemostatic properties, wound healing properties, and handling properties, including: hemostatic additives, such as gelatin, collagen, cellulose, chitosan, polysaccharides, starch, CMC; biologics based hemostatic agents such as thrombin, fibrinogen, and fibrin, additional biologics hemostatic agents include, without limitation, procoagulant enzymes, proteins and peptides, each such agent can be naturally occurring, recombinant, or synthetic, and may be further selected from the group consisting of fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, albumin, platelet surface glycoproteins, vasopressin and vasopressin analogs, epinephrine, selectin, procoagulant venom, plasminogen activator inhibitor, platelet activating agents, synthetic peptides having hemostatic activity; anti-infective agents, such as chlorhexidine gluconate (CHG), triclosan, silver, and similar anti-bacterial/microbial agents that are known in the art; additives that increase the stickiness of the hemostat; diluents, saline solutions, similar additives known in the art; derivatives of the above and any combination thereof.

In one embodiment, hemostatic powder and/or aggregates composition according to the present invention are made from oxidized cellulose-based fiber materials such as ORC or from pre-shredded oxidized cellulose-based materials.

In one embodiment of the invention, the powder composition has the property of forming a gel upon contact with blood. The formed gel has a resistance of equal to or higher than 10 times that of a gel formed upon contact of a comparative composition with blood.

In one embodiment a comparative powder composition consists of Oxidized Regenerated Cellulose (ORC) alone.

The term "gel" relates to a viscous and/or solid-like material that can have properties ranging from soft and weak to hard and tough. The gel can be a hydrogel.

Typically, a hydrogel is a network of polymer chains that are hydrophilic. Hydrogels can contain over 90% water and include polymeric networks.

The gel can be a clot being a thick mass of coagulated liquid, especially blood.

The term "contacting/contact" is used in its broadest sense and refers, for example, to any type of combining action which brings the hemostatic composition into sufficiently close proximity with the blood such that a clot or gel is formed.

The term "blood" includes blood fractions such as plasma.

In one embodiment, the comparative powder composition is composed of ORC fibers having a D90 value of less than 350 μm and a D50 value of less than 167 μm.

In one embodiment of the invention, the aggregates and/or powder composition according to the invention has the property of forming a gel upon contact with blood. The formed gel has a hemostatic capability of equal to or higher than 1.5 times that of a gel formed upon contact of a comparative aggregates composition with blood.

In one embodiment, the comparative aggregates composition is composed, for example, of ORC fibers having a D90 value of less than 350 μm and a D50 value of less than 167 μm.

In one embodiment, the comparative aggregates is composed, for example, of ORC fibers having a D90 value of less than 177 μm and a D50 value of less than 95 μm.

The term "resistance of a gel" relates to the results of the modified bloom test (as exemplified below) that demonstrate the force required by the metallic rod to pass through the gel at extension of 7 mm whilst moving at a speed of 5 mm/min. This force reflects the level of resistance of the gel (the greater the force, the higher the resistance of the gel) and in turn indicates what is the level of cohesive strength of a gel. The greater the force required for the rod to precede with its steady movement, the greater the resistance of the gel.

In a further aspect, the invention provides a method for forming a gel comprising the step of: contacting a hemostatic composition according to the invention with blood, thereby forming a gel.

In one embodiment, the method forms a gel having a resistance of equal to or more than 10 times or more than 12 times higher than that of a gel formed upon contact of a comparative composition with blood, and/or forms a gel having a hemostatic capability of equal to or more than 1.5 times higher than that of a gel formed upon contact of a comparative composition with blood.

In one embodiment, the comparative composition comprises cellulose-based fibers and lacks omega amino carboxylic acid at a concentration range of 2.5%-5.0% w/w of the entire composition; lacks protamine salt at a concentration range of 2.5%-5.0% w/w of the entire composition; and lacks a divalent cation, the cation concentration being 1.36-1.77% w/w of the entire composition.

In a further aspect, the invention provides a kit comprising a container including a hemostatic composition of the invention, and optionally an applicator, a carrier, and/or instructions for use. The term "carrier" relates to a physical matrix comprising and/or holding the hemostatic composition. Examples of carriers include, but are not limited to, pads for internal and/or external use such as cellulose-based pads, collagen-based pads; implants such as orthodontic and orthopedic implant; flowable sealants and/or hemostats such as SURGIFOAM®, EVICEL®.

In some embodiments, the container is an applicator.

In one embodiment, aggregate or powder composition with 5.0% $CaCl_2$, 2.5% PS and 2.5% εACA is equivalent to: 40 mg/cm$^2$ $CaCl_2$, 20 mg/cm$^2$ PS, 20 mg/cm$^2$ εACA.

For example, if a total amount of 100 mg final composition is applied on a circular punch having a diameter of 0.4 cm. The 100 mg composition was applied on the punch surface area which is $\pi*(0.2\ cm)^2=0.126\ cm^2$. Meaning that 793.65 mg/cm$^2$ (resulting from the calculation: 100 mg/0.126 cm$^2$) of final composition was used.

If $CaCl_2$ is used at a concentration of 5% of the final composition, therefore 793.65*0.05 equals to about 40 mg/cm$^2$.

If PS is used at a concentration of 2.5% of the final composition, therefore 793.65*0.025 equals to about 20 mg/cm$^2$.

If εACA is used at a concentration of 2.5% of the final composition, therefore 793.65*0.025 equals to about 20 mg/cm$^2$.

The hemostatic composition may have one or more of the following advantages over several known products:

1—can stop bleedings e.g. at large blood vessels suture line and therefore can significantly reduce and stop bleeding from blood vessels suture lines unlike several known products which have limited efficacy in achieving hemostasis in blood vessels;

2—can achieve hemostasis without the need for pressure application. Several known products require the application of pressure in order to achieve hemostasis (e.g. manually compressing with a gauze);

3—is activated in blood. When activated by moisture, the hemostatic fibers and/or aggregates gain structure (e.g. in the form of a clot/gel) and can achieve hemostasis. Several known products have pre-formed structural integrity;

4—can set in blood, does not float away easily and can achieves hemostasis. Several known products have limited efficacy in a wet environment;

5—can adhere to the bleeding site, yet still reversible i.e. adheres to the bleeding site and resists lavage, yet can be scraped off to remove and gain access if surgical correction is needed. Several known products have either limited adherence in a wet field or they cannot be easily removed once applied.

The hemostatic compositions can be used for various surgical and wound healing topical applications, such as anti-adhesion barriers, hemostats, tissue sealants, etc. The hemostatic compositions of the present invention can perform as a hemostat, as dry composition or as a composition in a paste form with superior hemostatic properties and good tissue conformability.

The hemostatic fibers and/or aggregates composition can be used for various surgical and/or wound healing topical applications, such as for anti-bactericidal treatment, hemostasis, anti-adhesion, sealing, and/or for minimizing or preventing leaks e.g. leaks from anastomotic sites such as leaks created during coronary artery bypass graft (CABG).

The composition may be used to stop bleeding in hard to reach areas e.g. during laproscopic surgery, on anastomotic sites such as CABG and/or arteriovenous anastomosis, procedures where applying pressure is unwarranted such as spinal surgery or neuronal surgery.

Patients that undergo coronary artery bypass graft (CABG) surgery may have leaks from the anastomotic sites created during the procedure. Many of these leaks are addressed during the surgery using either additional sutures or various hemostats. Stopping these leaks during surgery and preventing them from developing post operatively, will help surgeons be more confident that their patients will not have post-operative anastomotic leaks. Bleeding after CABG procedures requiring a transfusion or reoperation is associated with a significant increase in morbidity and mortality. In as many as 20% of cases, a specific site of bleeding can be identified, during the reoperation. The typical sources of surgical bleeding include cannulation sites, the proximal and distal anastomotic site, and the branches of the ITAs and vein grafts. According to literature, 2-3% of CABG patients will require re-exploration for bleeding and as many as 20% will have excessive post-operative bleeding requiring blood transfusion.

The content of all cited publications are hereby incorporated by reference in their entirety.

EXAMPLES

Materials and Methods.

TABLE 1A

Oxidized Regenerated Cellulose (ORC) Fibers.

| Oxidized Regenerated Cellulose (ORC) Fibers | Category |
|---|---|
| Long ORC Fibers | |
| Distribution: D90 of less than 350 μm and D50 of less than 167 μm* | Cellulose-based fibers |
| Fine ORC Fibers | |
| Distribution: D90 of less than 177 μm, and D50 of less than 95 μm* | Cellulose-based fibers |

*See below elaboration on the preparation.

TABLE 1B

Compounds used to supplement ORC Fibers.

| Compound | Category | Manufacturer | Cat. Number |
|---|---|---|---|
| Calcium Chloride dehydrate (CaCl$_2$) | Divalent cation salt | Merck | 1.42000.5000 |
| Protamine Sulfate (PS) | Protamine salt | Sigma | P3369-100G |
| 6-Aminocaproic acid (ε-aminocaproic acid = epsilon-aminocaproic acid = εAC A) | Omega amino carboxylic acid | Sigma | A204-100G |
| Chitosan | Positively charged polysaccharide | Sigma | 448869-50G |

TABLE 1B-continued

Compounds used to supplement ORC Fibers.

| Compound | Category | Manufacturer | Cat. Number |
|---|---|---|---|
| FeCl$_3$ | Trivalent cation | Sigma | 157740 |
| Lysine | Positively charged amino acid | Sigma | L5501 |

TABLE 2

% (w/w) of cation concentration equivalent in CaCl$_2$ and FeCl$_3$.

| Amount of indicated salt (w/w) | Amount of calcium cations (w/w) | Amount of Ferric cations (w/w) |
|---|---|---|
| 3.0% CaCl$_2$ | 0.818% | — |
| 3.5% CaCl$_2$ | 0.954% | — |
| 5.0% CaCl$_2$ | 1.363% | — |
| 6.0% CaCl$_2$ | 1.636% | — |
| 6.5% CaCl$_2$ | 1.768% | — |
| 3.0% FeCl$_3$ | — | 1.033% |

Oxidized Regenerated Cellulose (ORC) Fibers Preparation:

The manufacturing process of the ORC fibers started with ORC material SURGICEL® Original absorbable hemostat. ORC material was cut into 2.54-5.08 cm (1- to 2-inch) wide sections before the material was fed into a blade that cuts the fabric into smaller pieces. The cut ORC fabric pieces were then ground into ORC fine fibers by two consecutive milling processes (hammer milling and air classifier milling). The fibers from different milling steps were taken for future use in order to incorporate different fiber sizes in the final aggregates.

More specifically, the process for manufacturing the fibers comprised the steps of: slitting and cutting of SURGICEL® Original fabric; milling the resulting material using hammer milling; milling step(s) in an air classifier for obtaining long and fine fibers; and optionally mixing fibers of the different sizes. Different fiber sizes are fibers having different size distribution.

Slitting and cutting was carried out to slit and cut fabric into appropriate size pieces that are approximately 2.54 cm by 7.62 cm (1 inch by 3 inches). The main operations performed for slitting and cutting were to unwind a roll of fabric, slit the fabric into strips, cut the strips to size and deliver the cut pieces into the first milling step.

In a first milling step, processed pieces of cellulose-based fabric material were converted from an intermediate coarse fiber produced in the slitting and cutting step to a material having a D90 value of less than 452 μm and D50 value of less than 218 μm, while having minimal impact on the color index and water soluble content of the material. The machine used for milling at this step was a hammer mill type model WJ-RS-D6A manufactured by Fitzpatrick. The hammer mill was equipped with a 497 μm round screen and a set of blades that breaks down the fabric until it passes through the screen to produce intermediate coarse cellulose-based fibers. The parameters of the milling were: mill speed of about 7000 RPM; processing temperature of less than 80° C.; number of blades of 8 (2 impellers each); blade type of a 225 knife, impact type blades; blade orientation set as "impact".

Intermediate coarse fibers from the first milling step were fed at a controlled rate into the second mill. The intermediate coarse fibers were processed through the air classifier equipment three times in order to obtain the desired size. In addition, in certain experiments, fibers taken from the first run through the air classifier were extracted in order to incorporate different fiber sizes in the final aggregates.

At this step(s), a Quadro Air Classifier F10 was used with a milling speed of 8400 rpm, blower speed of 1800 rpm and 3 passes. After one pass, the resulting long ORC fibers had a D90 value of less than 350 μm and a D50 value of less than 167 μm. After 3 passes, the resulting fine ORC fibers had a D90 value of less than 177 μm and a D50 value of less than 95 μm.

Powder Composition Preparation.

All powders were weighed using an analytical balance in humidity controlled conditions. Relative humidity did not exceed 20% throughout the powder preparation process. All powders were comprised of ORC fibers having D90 of less than 350 μm and D50 of less than 167 μm, prepared as described above, and supplemented with different positively charged compound(s). A positively charged compound is a material containing a positively charged group/element within it. In examples 1-3 the ORC fibers of the powder or aggregates composition included fine ORC fibers; For example, if the compound was 3% $FeCl_3$ (w/w from the entire composition weight), the ORC fine fibers constituted 97% w/w. (see size distribution in table 1A); in example 4, the ORC fibers of the supplemented aggregates were a combination of 10.0% (w/w of the final mixture weight) long ORC fibers (see size distribution in table 1A) and 77.5-80.0% (w/w of the final mixture weight) fine ORC fibers. The supplementation of compound(s) to ORC fibers was up to 10.0% (w/w) in the in-vitro testing and up to 12.5% (w/w) in the in-vivo testing. All compounds, elaborated in the Table 1B, were provided in powder form.

Each fibers-compound(s) mixture combination was transferred to a mortar and pestle and mixed thoroughly until the powder particles were equally/homogenously distributed within the composition. To minimize adsorption of humidity, the powder compositions were stored in vials and sealed with a plastic paraffin film (PARAFILM®).

The compositions in Examples 1-2 were in powder form. In Example 3, the non-compacted composition was in powder form while the compacted compositions were in aggregate form. In Example 4, all compositions were in aggregate form (see elaboration on aggregate preparation below).

Aggregate Preparation.

To obtain aggregates/granules that contain a higher mass per volume ratio, two steps were carried out:

I— Powder compaction (capsulation); and
II— Capsule drying, milling/grounding and sieving.
See elaboration of steps I and II below.

Powder Compaction.

Compaction was carried out using a manual hydraulic press (Specac Atlas 15 tons model GS15011) and a suitable evacuable pellet die, the pellet die has a diameter of 10 mm (Specac GS03100). About 300 mg powder composition (prepared as described above) was loaded into the pellet die up to a height of approximately 1.5 cm-2.0 cm. In the next step, a metallic rod (which is part of the manual hydraulic press equipment) was fitted on top of the powder and used to reach a pressure of 4 tons (about 1.3 tons per cm$^2$) by the manual hydraulic press. Following this step, a capsule (compacted powder) in a diameter of 10 mm and a height of approximately 0.3 cm-0.5 cm was formed. The capsule was released from the pellet die and broken into smaller parts with a mortar and pestle to increase surface area for the next drying step.

Capsule Drying, Milling/Grounding and Sieving.

Capsule halves were dried in a vacuum oven (Cole Parmer vacuum oven model 05017-05) at 37° C. for approximately 16 hours to remove any excess humidity (and reach a humidity of less than 5% w/w). The dried capsule parts were ground/milled at 20,000 rpm for 30 seconds using IKA® Works, Inc. tube mill control 9737790. In the next step, the aggregates were vigorously sieved using an MRC (sieve manufacturer) sieve shaker (model LS-200 at intensity level 2) for 1 minute through a set of 2 sieves; one with a pore size of 420 μm and another with a pore size of 75 μm. The aggregates remaining between the two sieves were collected and stored at room temperature (20° C.-27° C.) in a tightly closed vial, sealed with plastic paraffin film until use. At the end of this stage, all the components present in each final granule/aggregate composition were homogenously distributed within it.

Blood Preparation.

Blood used in Examples 1-2 was collected from exterminated Porcines by Lahav contract research organization (C.R.O.) and delivered in chilled containers (4° C.). Upon blood collection, 5000 IU Heparin was added per liter of blood [Heparin Sodium-Fresenius 5000 IU/1 ml solution for injection; manufacturer: BODENE (PTY) LTD trading as Intramed; Cat. Number: 9207910LAB].

To prevent clotting, upon arrival additional Heparin was added (5000 IU per 1 liter blood). The heparinized blood was mixed gently by inverting the bottle several times. In the next step, to remove residual clots, the heparinized blood was filtered through a 20 μm polypropylene syringe filter (SVL25D20HQSA25 by Entegris) and collected into a polypropylene container (to prevent blood clotting induced by glass). The filtered heparinized blood was stored at 4° C. until use.

Bloom Test.

Bloom is a test used to measure the cohesive strength of a gel or gelatin. Cohesive strength represents the bonding between the molecules of a tested material/composition. Generally, Bloom test relates to determination of the force (in grams) which has to be applied to a free surface of 6.67% gelatin gel (prepared by dissolving 7.5 gr gelatin in 105 gr water) by means of a cylindrical piston (having a diameter of 12.7 mm) in order to produce a depression of 4 mm. For the test, the gel is typically formed in a glassware with the following dimensions: a capacity of 150 ml, an interior diameter of 59 mm, and a height of 85 mm. The speed of the descending piston is set to 30 mm/minute (see Bloom test described in U.S. Pat. No. 1,540,979).

In the Examples below, a modified Bloom test was carried out to test the cohesive strength of clots formed when different tested powder compositions were mixed with blood. This parameter was assessed as an indication of the potential hemostatic efficacy of each tested composition. Generally, a higher resistance force (a high value in the Bloom test) correlates with higher cohesive strength and suggests that the composition has a high hemostatic efficacy; low resistance force correlates with low cohesive strength and suggests that the composition has low hemostatic efficacy. The cohesive strength induced by each tested powder composition was evaluated on a comparative basis to the non-supplemented ORC fibers. The results are presented as fold increase in the resistance force relative to the non-supplemented ORC fibers.

The modified Bloom test was carried out as follows:
1) 300 mg of each tested powder composition was weighed into a 7 ml tube (interior diameter: 15 mm, height: 50 mm).
2) 2.5 ml of blood (prepared as described above under "Blood preparation") was added to each powder composition.
3) The tube was vortexed vigorously at 3200 rpm until no dry powder was visually apparent and the blood-powder composition mixture was incubated for 3 minutes to enable clot formation.
4) To measure the cohesive strength, the vial was placed in a 'Lloyd LF plus' instrument and a metallic rod [1.27 cm (0.5 inch)] was inserted into the vial at a constant pre-set descending speed: 5 mm/minute. The resistance force of the clot to the movement of the metallic rod at the point of 7 mm extension into the clot was measured in units of megapascal (MPa). The test was carried out at room temperature.

Suture Pre-Clinical Model.

A pulsatile ex-vivo cardiopulmonary bypass (CPB) model was used to simulate physiological conditions. The model is described in:

Sergeant, P., Kocharian, R., Patel, B., Pfefferkorn, M., & Matonick, J. (2016). Needle-to-suture ratio, as well as suture material, impacts needle-hole bleeding in vascular anastomoses. Interactive CardioVascular and Thoracic Surgery, 22(6), 813-816. doi:10.1093/icvts/ivw042.

Briefly, the pulsatile ex vivo cardiopulmonary bypass model used a series of pumps and chambers to create, control and maintain blood pressure throughout the system. The model consists of a reservoir to filter blood going into and returning from a porcine carotid artery, a computer-integrated data acquisition system, oxygenator and heat exchanger. Flow impedance and volume partitioning adjustments are present to allow for fine adjustment of blood volume flow and pressure control.

The blood loss from the suture placed in the porcine carotid artery was collected and weighed to establish a leak rate. The leak rate was calculated and recorded as the volume of blood collected over a period of time.

To simulate physiological conditions, the following parameters were used:
Pressure of 120/80 mmHg
Pulse rate of 72/min
Blood temperature of 33-35° C.

10,000 IU of heparin were added to 1 L of donor porcine blood and titrated with 10 mg/ml Protamine sulfate to adjust activated clotting time (ACT) to approximately 369 seconds. ACT was measured with a VetScan i-STAT Portable Handheld Unit (Abbott Point of Care) and an I-STAT ACT Celite Cartridge (Abbott Poing of Care, Part #:600-9006-10).

A porcine carotid artery was isolated from the surrounding tissue and mounted on the system. Tubing clamps were used to secure the tissue to the fittings. Blood flow on both sides of the carotid was restricted and the carotid was sutured in a simple continuous pattern with a 6-0 PROLENE Suture (8806H) and a BV-1 needle. Blood loss mass over 2 minutes was measured as a baseline.

The powder/aggregates were applied over the sutured sites and allowed to cure for 4 minutes following complete application. Restriction was removed and the blood loss mass over 2 minutes was measured.

Liver Biopsy Punch In-Vivo Model.

A mature, about 60 kg, female porcine was put on a fast for 24 hours prior to the surgical procedure. The animal was anesthetized with 1150 mg-1400 mg Ketamine, 115 mg-140 mg Xylazine, 7.5 mg Midazolam. Anesthesia was maintained with Isoflurane and the abdomen was opened to reveal the liver. Mean arterial blood pressure, body temperature and heart rate were continuously monitored throughout the surgical procedure. The experiment was terminated when mean arterial blood pressure dropped below 60 mmHg.

A 4 mm diameter×2 mm depth biopsy punch was carried out on the liver lobe and the specimen was excised with surgical scissors. The punch site was allowed to bleed for 30 seconds and bleeding intensity was visually assessed on a scale of 0-5; whereby no bleeding was given a score of 0 and intensive bleeding was given a score of 5. Then, the punch site was wiped with clean gauze to remove excess blood and 100 mg of the tested aggregate composition was poured into the punch cavity (for example, an aggregate composition with 5.0% $CaCl_2$, 2.5% PS and 2.5% εACA is equivalent to: 40 mg/cm$^2$ $CaCl_2$, 20 mg/cm$^2$ PS, 20 mg/cm$^2$εACA).

A total amount of 100 mg final composition is applied on a circular punch having a diameter of 0.4 cm. Therefore, the 100 mg composition was applied on the punch surface area which is $\pi*(0.2 cm)^2$ about 0.126 cm$^2$. Meaning that 793.65 mg/cm$^2$ (resulting from the calculation:100 mg/0.126 cm$^2$) of final composition was used.

$CaCl_2$ is used at a concentration of 5% of the final composition, therefore 793.65*0.05 equals to about 40 mg/cm$^2$.

PS is used at a concentration of 2.5% of the final composition, therefore 793.65*0.025 equals to about 20 mg/cm$^2$.

εACA is used at a concentration of 2.5% of the final composition, therefore 793.65*0.025 equals to about 20 mg/cm$^2$.

Mild pressure was manually applied over the composition using clean gauze for 1 minute. Bleeding was monitored over a period of 4 minutes, after which bleeding intensity was rated again on a scale of 0-5. The results are presented as percentage of complete hemostasis rate achieved from all replicates.

Example 1: The Effect of Different Compounds on the Cohesive Strength of a Clot Formed with Fine ORC Fibers The purpose of this Example was to examine the cohesive strength induced by ORC fibers supplemented with different compounds. For this purpose, a modified Bloom test was carried out as described above.

The tested powder compositions comprised of fine ORC fibers supplemented with different compounds as shown in FIG. 1. The powders were prepared as described in the Materials and Methods section under "Powder Preparation". Table 2 above shows the percentage (w/w based on the entire weight composition) of cations in $CaCl_2$ and $FeCl_3$ used in all the experiments below. FIG. 1 is a bar graph showing the fold increase of the resistance force/cohesive strength obtained for the different tested powder compositions as compared to non-supplemented fine ORC fibers.

Results of the modified bloom test demonstrate the force required by the metallic rod to pass through the gel, formed with the tested composition upon contact with blood, at extension of 7 mm whilst moving at a speed of 5 mm/min. This force reflects the level of resistance of the gel (the greater the force, the greater the resistance of the gel) and in turn indicates what is the level of cohesive strength of a gel. Cohesive strength represents the strength by which molecules of a composition are bound together. The more force required for the rod to proceed with its steady movement, the greater the resistance of the gel is.

The results show that supplementation of fine ORC fibers with 3% Ferric Chloride ($FeCl_3$) had a significant positive effect on the resistance of the formed clots.

It was also shown that supplementation of fine ORC fibers with either 3% or 6% calcium chloride ($CaCl_2$) increased the resistance force in a dose dependent manner.

When comparing the efficacy of 3% $CaCl_2$ supplementation with compositions that were further supplemented with either 3% PS; or 3% PS and 3% εACA; or 3% PS and 3% chitosan, the results indicated that there was an improvement in the resistance force of the further supplemented compositions. Including 3% lysine (Lys) in the composition had a negative effect and decreased the resistance force obtained (compare fine ORC fibers supplemented with 3% $CaCl_2$ and 3% PS vs. fine ORC fibers supplemented with 3% $CaCl_2$, 3% PS and 3% Lys in FIG. 1).

It can be concluded that adding specific positively charged compound(s) such as calcium chloride, protamine sulfate (PS) and/or chitosan to ORC fibers improves the cohesive strength induced by the fibers, suggesting that these supplemented composition may have a beneficial hemostatic effect in-vivo.

Without being bound by the mechanism, supplementing ORC fibers with specific positively charged compounds (e.g. different cations e.g. divalent cations provided by $CaCl_2$, protamine salt e.g. protamine sulfate or positively charged polysaccharide e.g. chitosan and an omega amino carboxylic acid e.g. εACA) increases the cohesive strength of a gel formed by the hemostatic powder composition.

Example 2: The Effect of Supplementation Combinations on the Cohesive Strength Induced by a Powder Composition The previous Example indicated that supplementation of fine ORC fibers with 6% $CaCl_2$ resulted in a higher resistance force/cohesive strength as compared to 3% $CaCl_2$. The previous Example showed that further supplementation of 3% $CaCl_2$-fine ORC fibers composition with additional positively charged compounds increased the cohesive strength of the composition. Therefore, in this Example the contribution of further supplementation of a composition of fine ORC fibers with high $CaCl_2$ concentrations (5% or 6%) with additional positively charged compounds, to the cohesive strength was tested. The results are shown in FIG. 2.

Similar to the results shown in the previous Example, supplementation of 6% $CaCl_2$—ORC mixture resulted in an increase in resistance force/cohesive strength as compared to ORC only. It was found that the improved resistance force demonstrated in clots formed by supplementation of 6% $CaCl_2$, was abolished in clots formed by supplementation of 6% $CaCl_2$ mixture with Lysine (Lys). Additional supplementation of 6% $CaCl_2$—ORC with Arginine (Arg) had the same negative effect.

Supplementation of ORC fibers with either 3% chitosan or 3% protamine sulfate (PS), further to 6% $CaCl_2$, demonstrated an increase in the clots' resistance force.

Figure 2:
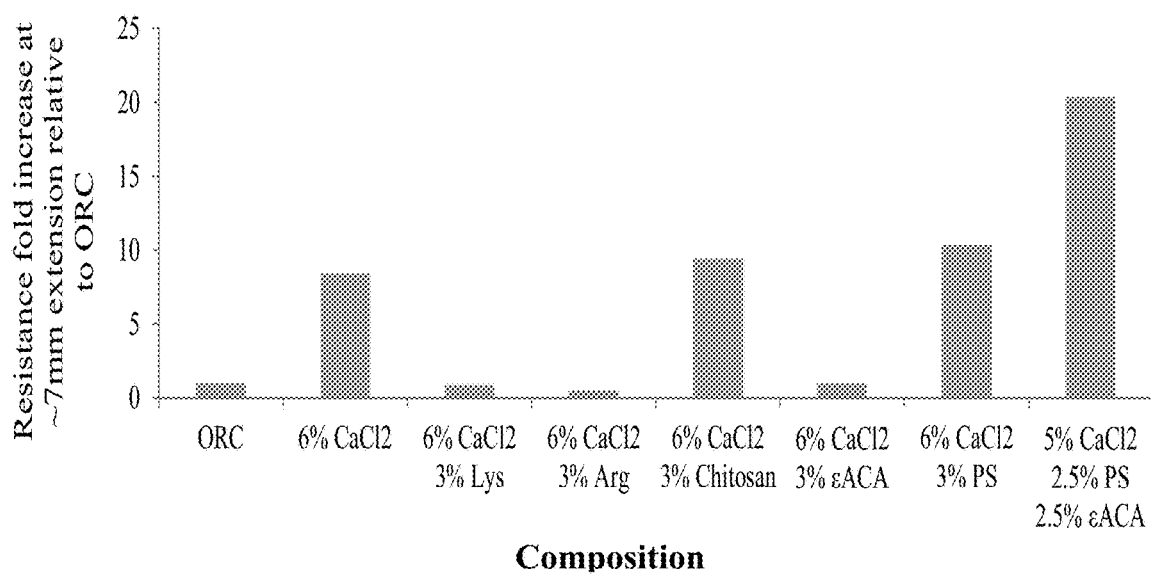

Furthermore, further supplementation of the 6% $CaCl_2$ ORC composition with 3% εACA alone decreased the resistance of the clots (compare fine ORC fibers supplemented with 6% $CaCl_2$ vs. fine ORC fibers supplemented with 6% $CaCl_2$ and 3% εACA in FIG. 2).

Superior results were obtained with ORC supplemented with 5.0% $CaCl_2$, 2.5% PS and 2.5% ε-aminocaproic acid (εACA).

These results suggest that only specific compounds and specific combinations thereof and concentrations improve the cohesive strength properties induced by ORC fibers.

Example 3: The Hemostatic Effect of Different Compositions in an Ex-Vivo Model

In this Example, an exemplary composition with high cohesive strength according to the in-vitro tests was examined for its hemostatic capability in a suture (pre-clinical) ex-vivo model (as described in the Material and Methods section). The composition's efficacy was tested in the form of a powder or as aggregates. Also, the effect of the absence of calcium from the composition on the hemostatic efficacy was evaluated.

Powder compaction was carried out as detailed under "Powder compaction" (Material and Methods section); the compacted powder was then subjected to a step of drying and a step of milling/grounding as detailed under "Capsule drying and milling/grounding", thereby creating powder granules/aggregates.

Blood loss volumes before and after composition application on a suture site were compared in the manner described above ("suture pre-clinical ex-vivo model").

For these purposes, a powder composition of fine ORC fibers supplemented with 5.0% $CaCl_2$, 2.5% PS and 2.5% εACA was tested in both a compacted and non-compacted form; and a compacted composition of fine ORC fibers supplemented with 5.0% PS and 5.0% εACA (without calcium) was also evaluated.

Figure 3:
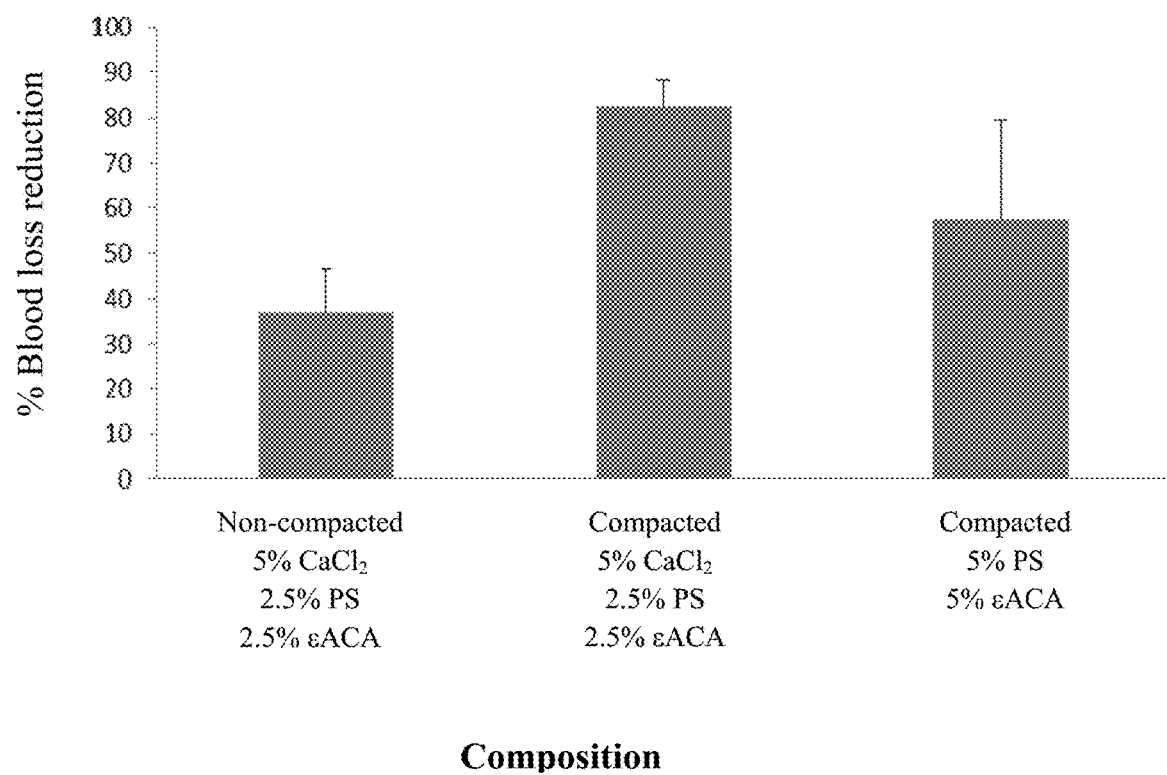
FIG. 3 is a bar diagram showing the hemostatic efficacy of a non-compacted and compacted powder composition (i.e. composition in the form of aggregates) and the effect of calcium ions in the compacted composition by an ex-vivo suture model.

As demonstrated in FIG. 3, there is a general trend of improved hemostatic efficacy when the powder is compacted milled and sieved into aggregate form (an increase in % blood loss reduction was observed). The results also show the positive contribution of calcium chloride to the efficacy of the ORC powder.

Example 4: The Effect of Compound Concentration Range in the Aggregates Composition on the Hemostatic Efficacy, Determined by In-Vivo Tests The following example examines the in-vivo hemostatic effect of changing the concentrations of each of the compounds chosen according to the above Examples. The results were collected from different pre-clinical experiments carried out on a female porcine using a Liver Biopsy Punch in-vivo model as described above. The results of each experiment are presented in a different table—tables 3, 4 and 5. In this experiment various aggregates compositions were tested. The aggregate compositions tested were ORC fibers with or without supplementation with compounds, the concentrations of the compounds are specified in the Tables below. The compound-supplemented aggregates included ORC fibers combinations of 10.0% (w/w of the final mixture weight) long ORC fibers (see size distribution in table 1A) and 77.5-85.0% fine ORC fibers.

The table lists success rates of complete bleeding arrest/complete hemostasis. In each experiment, fine ORC aggregates (without any supplementation) served as a baseline control to examine the hemostatic efficacy of the supplementation of the compounds to ORC fibers.

Tables 3, 4 and 5: Complete Hemostasis Rate Obtained after Application of Aggregates Compositions in a Liver Biopsy Punch In-Vivo Model (Number of Replicates in Each Tested Composition≥3).

| Composition Ratio | Complete Hemostasis Rate |
|---|---|
| Fine ORC | 25% |
| 2.5:95 PS:ORC | 0% |
| 2.5:95 εACA:ORC | |
| 5:92.5 CaCl$_2$:ORC | 25% |
| 2.5:92.5 εACA:ORC | |
| 5:92.5 CaCl$_2$:ORC | 0% |
| 2.5:92.5 PS:ORC | |
| 5:90 CaCl$_2$:ORC | 75% |
| 2.5:90 PS:ORC | |
| 2.5:90 εACA:ORC | |

| Composition Ratio | Complete Hemostasis Rate |
|---|---|
| Fine ORC | 0% |
| 3.5:91.5 CaCl$_2$:ORC | 0% |
| 2.5:91.5 PS:ORC | |
| 2.5:91.5 εACA:ORC | |
| 6.5:88.5 CaCl$_2$:ORC | 37.5% |
| 2.5:88.5 PS:ORC | |
| 2.5:88.5 εACA:ORC | |

| Composition Ratio | Complete Hemostasis Rate |
|---|---|
| Fine ORC | 25% |
| 5:91.5 CaCl$_2$:ORC | 20% |
| 1:91.5 PS:ORC | |
| 2.5:91.5 εACA:ORC | |
| 5:90 CaCl$_2$:ORC | 50% |
| 2.5:90 PS:ORC | |
| 2.5:90 εACA:ORC | |
| 5:87.5 CaCl$_2$:ORC | 40% |
| 5:87.5 PS: ORC | |
| 2.5:87.5 εACA:ORC | |
| 5:91.5 CaCl$_2$:ORC | 20% |
| 2.5:91.5 PS:ORC | |
| 1:91.5 εACA:ORC | |
| 5:87.5 CaCl$_2$:ORC | 60% |
| 2.5:87.5 PS:ORC | |
| 5:87.5 εACA:ORC | |

Results presented in Tables 3-5 reaffirm that each compound is necessary for improving the hemostatic efficacy of ORC fibers since a composition that contained all three compounds (calcium chloride, PS and εACA) was notably superior compared to the other aggregates compositions. The results showed that for both PS and εACA a superior supplementation range is 2.5% to 5.0%. The range in which calcium chloride serves as a beneficial compound is between 5.0% and 6.5% (a cation concentration range of 1.363%-1.636% w/w).

The results show that the supplemented ORC is at least 1.5 times more efficient than ORC alone (37.5% complete hemostasis rate for supplemented ORC vs. 25% complete hemostasis rate for ORC alone).

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. A method of treating a bleeding wound, a bacterial infection at a wound site, minimizing or preventing a leak from an anastomotic site; sealing a leak at a site and/or preventing adhesion at a surgery site in a subject in need, the method comprising a step of applying onto and/or into the wound and/or site of the subject an effective amount of a hemostatic composition comprising: (i) cellulose-based fibers having a size distribution of D90 of less than 350 μm, and D50 of less than 167 μm, the fibers being at a concentration range of 83.5%-90.0% w/w of the entire composition; (ii) an omega amino carboxylic acid at a concentration range of 2.5%-5.0% w/w of the entire composition; (iii) protamine salt at a concentration range of 2.5%-5.0% w/w of the entire composition; (iv) a divalent cation, the cation concentration being 1.3%-1.8% w/w of the entire composition, wherein the composition is in the form of a powder and/or aggregates.

2. The method according to claim 1, wherein the applying step is carried out without applying pressure on the composition towards the wound and/or site.

3. The method according to claim 1, wherein the cellulose-based fibers comprise Oxidized Cellulose (OC) or Oxidized Regenerated Cellulose (ORC) fibers.

4. The method according to claim 1, wherein the omega amino carboxylic acid is Epsilon Amino Caproic Acid (εACA).

5. The method according to claim 1, wherein the protamine salt is protamine sulfate.

6. The method according to claim 1, wherein the divalent cation salt is provided by calcium chloride.

7. The method according to claim 6, wherein the concentration ranges of εACA, protamine sulfate, and calcium chloride are 2.5%-5.0%, 2.5%-5.0%, 5.0%-6.5% w/w, respectively, and wherein the remaining weight is contributed by the cellulose-based fibers to a total weight of 100% w/w.

8. The method according to claim 1, wherein a gel formed from the powder composition upon contact with blood has a resistance of equal to or higher than 10 times that of a gel formed upon contact of a comparative powder composition consisting of ORC with blood; and/or wherein a gel formed from the aggregates composition has a hemostatic capability of equal to or higher than 1.5 times that of a gel formed upon contact of a comparative aggregates composition consisting of ORC with blood.

9. The method according to claim 1, wherein the composition is in the form of aggregates having a size in the range of 75 μm-420 μm.

* * * * *